United States Patent [19]

Fages et al.

[11] Patent Number: 5,366,532
[45] Date of Patent: Nov. 22, 1994

[54] FERTILIZERS CONTAINING MICROORGANISMS AND THEIR PRODUCTION PROCESSES

[75] Inventors: Jacques Fages, Portet sur Garonne; Jacques Rigal, Toulouse; Daniel Mulard, Cugnaux, all of France

[73] Assignee: Lipha, Lyonnaise Industrielle, Lyon, France

[21] Appl. No.: 434,698

[22] PCT Filed: Feb. 25, 1988

[86] PCT No.: PCT/FR88/00106

§ 371 Date: Oct. 27, 1989

§ 102(e) Date: Oct. 27, 1989

[30] Foreign Application Priority Data

Feb. 27, 1987 [FR] France .................. 87 02634

[51] Int. Cl.$^5$ .................................................. C05F 11/08
[52] U.S. Cl. .................................................. 71/6; 71/7; 71/64.07; 71/64.08; 435/177; 435/180
[58] Field of Search ............ 71/6, 7, 64.07, 64.08; 435/177, 180

[56] References Cited

U.S. PATENT DOCUMENTS

| | | | |
|---|---|---|---|
| 4,155,737 | 5/1979 | Dommergues et al. | 71/6 X |
| 4,421,544 | 12/1983 | Jones et al. | 71/7 |
| 4,547,463 | 10/1985 | Sakata et al. | 435/180 |
| 4,774,186 | 9/1988 | Schaefer, Jr. et al. | 71/6 X |
| 4,798,786 | 1/1989 | Tice et al. | 435/177 |

FOREIGN PATENT DOCUMENTS 0083267 7/1983 European Pat. Off. .
3417899 11/1985 Germany .

*Primary Examiner*—Ferris Lander
*Attorney, Agent, or Firm*—Millen, White, Zelano & Branigan

[57] ABSTRACT

Fertilizer containing microorganisms of the rhizosphere packaged by microencapsulation in a polysaccharide matrix. The inoculum obtained after microencapsulation can be mixed with a granular solid fertilizer, then stored, or with a liquid fertilizer immediately before spreading.

20 Claims, 1 Drawing Sheet

ENCASEMENT OF AZOSPIRILLUM

SURVIVAL IN NITROGENOUS SOLUTION SOLONIA S390

LEGEND
A. LIPOFERUM CRT I

FERTILIZERS CONTAINING MICROORGANISMS AND THEIR PRODUCTION PROCESSES

BACKGROUND OF THE INVENTION

This invention relates to fertilizers containing microorganisms and process for producing such fertilizers.

It is known that plants cultivated on a large scale maintain a microflora consisting, for example, of bacteria for fixing nitrogen associated with their roots and that these rhizospheric microflora have an effect of promoting plant growth.

By adding an inoculum of a bacteria of the rhizosphere, a modification of the root development is observed (elongation, dry weight, degree of branching, number of absorbent hairs), a modification of the total dry matter and an increase in the grain yield. These effects are probably due to a combination of several phenomena such as nitrogen fixation, production of plant growth hormones, and pectinolytic activities that make better mineral absorption possible. The influence of the addition of bacteria inocula in the rhizosphere of plants is described, for example, in the article by Gaskins, M. H., Albrecht, S. L. and Hubbel, D. H. Agric. Ecos. Environ. 1984 (12), pp 99–116.

The methods used by the researchers: inoculation in liquid or granular form independently of any other agricultural practice is hard to achieve in the field because of the extra work it would impose on farmers. It has been proposed for cultivation of leguminous plants to package some inocula on some peat and to coat the seeds with the product obtained, but this process has the drawback of putting the microorganisms in direct contact with the different pesticides that generally coat grains. Now, these pesticides most often exhibit a high toxicity with respect to most bacteria species.

It would be advantageous to be able to mix fertilizers and the inocula of rhizosphere bacteria because it has been shown that the effect of an inoculation was better in the presence of mineral, and in particular nitrogenous, fertilizers. Actually, plants having good mineral nutrition exhibit a great deal of root exudation, which promotes the development of rhizospheric microflora. However, up to now the difficulty has been encountered that the inocula did not have sufficient viability upon contact with the fertilizer.

SUMMARY OF THE INVENTION

Figure 1:
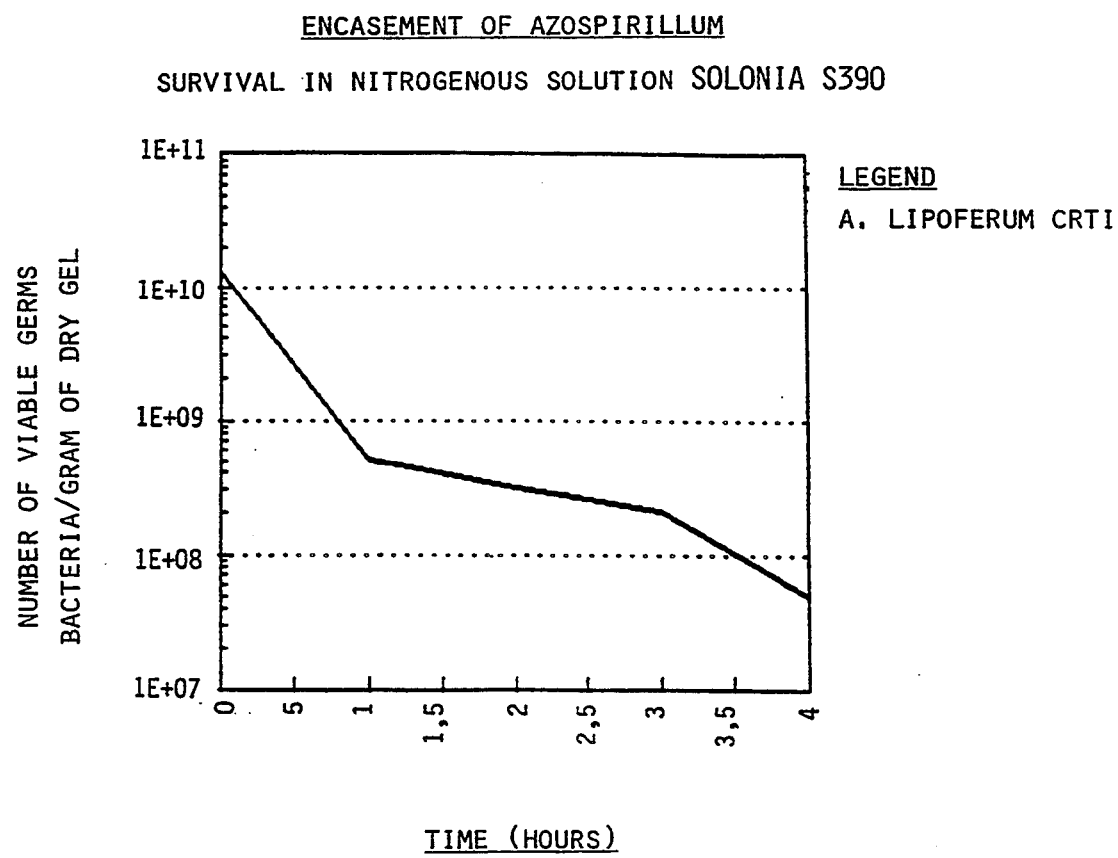
FIG. 1 illustrates the survival of Azospirillum left in contact with a medium containing a nitrogeneous solution of SOLONIA S390.

According to this invention, a form of inoculum has been found that has sufficient viability, upon contact with the fertilizer, for direct use in the field. More specifically, this invention relates to a fertilizer containing microorganisms isolated from the rhizosphere packaged by microencapsulation in a polysaccharide.

Processes of microencapsulating microorganisms in a polysaccharide matrix are already known, in particular from patents EP-A-017,565 and EP-A-083,267. Another usable process according to this invention consists in:

preparing a culture of microorganism in a fermenter in the presence of oxygen, stopping the oxygen supply and adding, preferably with agitation, polysaccharide to the culture medium, applying, on the surface of the mixture, an excess pressure of about 0.2 to 1.9 bars, depending on the type and concentration of polysaccharide added, introducing the mixture, under pressure, into a device comprising at least one calibrated nozzle with a diameter of about 0.1 to 0.8 mm, spraying the mixture, with the nozzle, in the form of drops into a mineral salt solution, rinsing and drying the gel obtained to obtain a storable inoculum.

The mineral salt used in this process can be, in particular, a salt such as chloride or sulfate of iron, manganese, aluminum, calcium, zinc or copper.

The encapsulated microorganism is generally in the form of a light beige powder able to be mixed with any fertilizer containing nitrogen and/or phosphorus and/or potassium. It more advantageously mixed with nitrogenous fertilizers such as ammonium nitrate or urea.

The fertilizer can be in solid form, in suspension or in liquid form. In the case of a solid fertilizer, the granular fertilizer can, for example, be mixed with the powder of the microencapsulated inoculum in a drum until the mixture is homogeneous. The respective quantities of fertilizer and microencapsulated inoculum are generally such that the weight ratio of the fertilizer to the microencapsulated inoculum is between about 500 and 2,000. Then a coating product such as an amine, a natural wax or a synthetic wax can be sprayed on the granules of fertilizer.

The coating product notably has the advantage that, when used in this invention, it efficiently achieves a homogeneous adhesion of the inoculum. The fertilizer according to the invention can then be stored.

In the case where the fertilizer is in suspension or solution, the fertilizer and inoculum are mixed immediately before application, then the entire unit is applied on the field to be fertilized.

The examples given below in a nonlimiting way will make it possible to better understand the invention.

EXAMPLE 1

Azospirillum lipoferum, a microorganism isolated from the rhizosphere of corn, is cultured in a medium containing, per liter:

| | |
|---|---|
| $MgSO_4, 7H_2O$ | 200 mg |
| NaCl | 100 mg |
| $CaCl_2$ | 20 mg |
| $FeSO_4, 7H_2O$ | 10 mg |
| $Na_2MoO_4, 2H_2O$ | 2 mg |
| yeast extract | 3 mg |
| $KH_2O_4$ | 400 mg |
| $K_2HPO_4$ | 600 mg |
| glucose | 30 g |
| $NH_4Cl$ | 5 g |
| $H_2O$ | qsp liter |

The air throughput and the agitation speed are such that the dissolved oxygen concentration is 30%. The starting pH being 6.8, it develops to 7.1 then is kept at this value by adding 1N soda.

The microencapsulation of this inoculum is performed with a solution of sodium alginate at the rate of 10 g/l. The mixture is stirred at a speed of 600 rpm. The solution is subjected to a pressure of 0.5 bars, then it is dispersed in a $CaCl_2$ solution at 6 g/l.

The gel obtained is rinsed with water, then it is oven-dried at a temperature of 30° C. with a relative humidity of 30%.

EXAMPLE 2

A quantity A of the microencapsulated inoculum of example 1 is mixed for about 5 minutes with a quantity B of granular ammonium nitrate in a granulation drum. The weight ratio B/A is 1,000. A quantity C of an aminated oil sold under the name LILAMINE AC 81L is sprayed on the granules thus obtained. In solidifying, this amine comes to coat the ammonium nitrate granules and a homogeneous adhesiveness of the inoculum is obtained. The weight ratio of A/C is 1.

Then the number of viable bacteria is measured according to the following protocol:

2 g of ammonium nitrate is dissolved in 500 ml of sterile distilled water. The powdered inoculum is collected by filtration on a filter with a 0.45-micrometer porosity.

the filter is placed in 50 ml of phosphate buffer having the following composition:

| | |
|---|---|
| $KH_2PO_4$ | 3.336 g |
| $Na_2HPO_4$ | 18.773 g |
| $H_2O$ | qsp 1 liter | and having a pH of 7.2. The polysaccharide is decrosslinked in a buffer solution.

This operation is facilitated by putting the flask used on an orbital agitating table for 1 hour. Decimal dilutions are spread on a Petri dish and the colonies that have appeared after incubation for 48 to 72 hours at a 35° C. temperature, the optimal temperature for growth of Azospirillum lipoferum, are counted.

The following viability is observed:

$1.6 \times 10^9$ viable cells after 26 hours of storage.
$1.5 \times 10^9$ viable cells after 3 days of storage.
$0.7 \times 10^9$ viable cells after 9 days of storage.
$0.3 \times 10^9$ viable cells after 1 month of storage.

EXAMPLE 3

The microencapsulated inoculum of the example is left in contact in a nitrogenous solution sold under the name SOLONIA S 390 having the following composition by weight:

| | |
|---|---|
| $CO(NH_2)_2$ | 33.2% |
| $NH_4NO_3$ | 41.5% |
| $H_2O$ | 25.3% |

The solution containing the bacteria is filtered as is and at regular intervals the residual viability of the bacteria is measured according to the protocol of example 2. The accompanying curve illustrates the survival of bacteria in such a medium.

It is interesting to note that most of the liquid spreaders empty in about 0.5 hours. As a result, the inoculum can be spread while it exhibits a high viability compatible with the doses used during bacterial inoculation in the field.

We claim:

1. A mixture of fertilizer and a minor amount of microorganisms isolated from the rhizosphere, said microorganisms being packaged by microencapsulation in a polysaccharide matrix.

2. A fertilizer mixture according to claim 1, in which the microencapsulation is performed according to a process comprising:
   preparing a culture of microorganism in a fermenter in the presence of oxygen,
   stopping the oxygen supply and adding polysaccharide to the culture medium,
   applying, on the surface of the mixture, an excess pressure of 0.2 to 1.9 bars,
   introducing the mixture under pressure into a device comprising at least a calibrated nozzle with a diameter of 0.1 to 0.8 mm,
   spraying the mixture, with the nozzle, in the form of drops into a mineral salt solution,
   rinsing and drying the gel obtained to obtain a storable inoculum.

3. A fertilizer according to claim 1, characterized in that it is in solid form.

4. A fertilizer mixture according to claim 3, wherein the fertilizer is a nitrogenous fertilizer.

5. A fertilizer mixture according to claim 4, wherein the weight ratio of the fertilizer to the microencapsulated microorganism is between about 500 and 2000.

6. A fertilizer mixture according to claim 3, wherein the fertilizer is granular, said mixture being provided with a coating resulting in a product having a homogeneous adherence of the microencapsulated microorganism on the granular fertilizer.

7. A fertilizer mixture according to claim 6, wherein the coating is an amine or wax.

8. A fertilizer mixture according to claim 6, wherein the coating is an aminated oil.

9. A fertilizer mixture according to claim 8, wherein the mixture is homogenous, the fertilizer is nitrogenous, and the weight ratio of the fertilizer to the microencapsulated microorganism is between about 500 and 2000.

10. A fertilizer mixture according to claim 9, wherein the microorganism comprises *Azospirillum lipoferum*.

11. A fertilizer mixture according to claim 1, wherein the fertilizer is in liquid form.

12. A fertilizer mixture according to claim 11, prepared by mixing said fertilizer and the microencapsulated microorganisms immediately before spreading.

13. A fertilizer mixture according to claim 12, wherein the fertilizer is a nitrogenous fertilizer.

14. A fertilizer mixture according to claim 13, wherein the weight ratio of the fertilizer to the microencapsulated microorganism is between about 500 and 2000.

15. A fertilizer mixture according to claim 13, wherein the microorganism comprises *Azospirillum lipoferum*.

16. A fertilizer mixture according to claim 1, wherein the fertilizer is a nitrogenous fertilizer.

17. A fertilizer mixture according to claim 16, wherein the weight ratio of the fertilizer to the microencapsulated microorganism is between about 500 and 2000.

18. A fertilizer mixture according to claim 16, wherein the microorganism comprises *Azospirillum lipoferum*.

19. A fertilizer mixture according to claim 1, wherein the weight ratio of the fertilizer to the microencapsulated microorganism is between about 500 and 2000.

20. A fertilizer mixture according to claim 1, wherein the microorganism comprises *Azospirillum lipoferum*.

* * * * *